United States Patent
Solyntjes et al.

[19]

[11] Patent Number: 5,991,072
[45] Date of Patent: *Nov. 23, 1999

[54] LIGHT FILTERING LENS FILM

[75] Inventors: Alan J. Solyntjes, Richfield; Frank J. Fabin, Eagan, both of Minn.

[73] Assignee: 3M Innovation Properties Company, St. Paul, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/788,493

[22] Filed: Jan. 28, 1997

[51] Int. Cl.$^6$ .................................. G02B 5/20; F21V 9/06
[52] U.S. Cl. ......................... 359/361; 359/350; 359/360; 351/44; 2/8
[58] Field of Search ..................................... 359/350, 359, 359/360, 361; 351/44, 45, 47; 2/8, 427, 431

[56] References Cited

U.S. PATENT DOCUMENTS

| | | | |
|---|---|---|---|
| 1,176,313 | 3/1916 | Pfund | 359/360 |
| 3,112,490 | 12/1963 | Malcom, Jr. | 359/361 |
| 3,398,040 | 8/1968 | Allen et al. | 359/360 |
| 3,681,179 | 8/1972 | Theissen . | |
| 3,718,533 | 2/1973 | Shibata | 359/360 |
| 3,868,727 | 3/1975 | Paschall . | |
| 3,891,486 | 6/1975 | Willdorf | 359/360 |
| 4,169,655 | 10/1979 | Jacobson . | |
| 4,373,212 | 2/1983 | West . | |
| 4,707,860 | 11/1987 | Holmström . | |
| 5,118,540 | 6/1992 | Hutchison | 359/360 |
| 5,170,501 | 12/1992 | White | 2/8 |

FOREIGN PATENT DOCUMENTS

| | | |
|---|---|---|
| 0 597 391 A1 | 5/1994 | European Pat. Off. . |
| 08133792 | 5/1996 | Japan . |
| 2 162 960 | 2/1986 | United Kingdom . |
| 2 198 547 | 6/1988 | United Kingdom . |

OTHER PUBLICATIONS

Product information, "A Weldor Who Can See More Can Do More," Omni–View™ gold–plated welding filter plates by Gentex, Gentex Corporation, 1975.
Product information, "What You See is What You Weld. . .In Color," Gentex® Omni–View, Gentex Corporation, 1977.
American Society of Safety Engineers, American National Standard Practice for Occupational and Educational Eye and Face Protection, American National Standards Institute, Inc., Feb. 2, 1989,.
Product information guide, "AOTUFFMASTER™ Faceshield/Headgear System," Cabot Safety Corporation, 1992.
3M Product Performance Guide for Scotchtint™ and Scotchtint™ Plus Window Films, 3M Construction Markets Division, 1994.
Product information, "ELVEX® Specialty Face Protection," Elvex Corporation.
Product information guide, Chemgard® Faceshield Frames, Universal Visors, Noisefoe® Mark V. Ear Cup Kit for Slotted V–Gard Caps and Noisefoe® Mark IV Ear Cup Kit for Non–Slotted V–Gard Hats.

*Primary Examiner*—Cassandra Spyrou
*Assistant Examiner*—Darren E. Schuberg
*Attorney, Agent, or Firm*—James A. Rogers

[57] ABSTRACT

A lens film is used in filtering visible, infrared, and ultraviolet light. The lens film has one or more metallized layers stacked together. Each metallized layer has a substrate with a metal coating covering one face of the substrate. One or more protecting layers are disposed over the stack of metallized layers to provide protection film. The lens film also has an ultraviolet absorbing material, such as an ultraviolet absorbing binder or substrate material. The lens film can be configured so that it meets the American National Standards Institute's shade standards for protection from harmful or intense light. The lens film can be mounted on a lens of an eye protection device. One method of mounting the lens is to provide an adhesive layer over a portion of the lens film and then binding the lens film to the lens with the adhesive layer.

25 Claims, 7 Drawing Sheets

LIGHT FILTERING LENS FILM

FIELD OF THE INVENTION

The present invention relates to a light filtering device for absorbing and/or reflecting visible, ultraviolet, and infrared light. In particular, the present invention relates to a light filtering lens film having multiple layers.

BACKGROUND OF THE INVENTION

Many activities require eye protection due to the presence or creation of harmful visible, ultraviolet, and infrared light. One example of such an activity is welding where intense light is generated by the welder's torch and the heated metal. Current safety standards for industrial eye and face protection for welding and other activities are published by the American National Standards Institute, Inc. (ANSI) in *American National Standard Practice for Occupational and Educational Eye and Face Protection*, ANSI Z87-1-1989, incorporated herein by reference.

The ANSI standards define a set of shade ratings between 1 and 14 based on the weighted transmittance of luminous (380–780 nm), far ultraviolet (200–315 nm), near ultraviolet (315–385 nm), infrared (780–2000 nm), and blue (400–1400 nm) light. The ANSI standards also indicate the minimum shade protection recommended for certain specific activities. For electric arc welding, a protective lens should have a shade rating of 10–14, for gas welding, shades 4–8 are recommended, and for cutting or torch brazing, shades 3–6 are recommended.

In meeting these standards, those engaged in these hazardous light-generating activities must often wear eye protection devices which are extremely limiting and usually dedicated to that particular activity. For example, a welder typically has a special helmet, mask, or pair of goggles that is worn only while welding. Furthermore, such a helmet, mask, or goggles often provides only a limited range of vision as the protective lenses of the eye protection device have only a small viewing area.

These features of current eye protection devices are inconvenient for many wearers. For example, a worker on a job such as bridge repair, where welding is only one of the necessary activities, would find it convenient to have an eye protection device that could be used for both welding and other activities. Unfortunately, the lens shades required for eye protection devices appropriate for welding are usually too dark for other activities. Thus, there is a need for an eye protection device that can be used with activities that generate harmful light irradiation and can still be used with other activities that do not require such extreme light shielding.

In addition, workers must often wear other protective gear such as respirators which may not be conveniently or cost-effectively combined with current protective helmets, masks, or goggles. There is a need for a lightweight, low-cost light filtering device that can be used in conjunction with other protective gear without requiring that such gear be dedicated for use only with harmful light-generating activities.

The light filtering lens films of the present invention address these needs. The lens films of the present invention can be mounted on the lens or lenses of existing eye protection devices and are often detachable from these physical eye protection devices so that a worker can continue to wear the physical eye protection device while engaged in other activities. The lens films of the present invention provide a convenient, lightweight, low cost product for protecting wearers from harmful light arising from a wide variety of sources.

SUMMARY OF THE INVENTION

The present invention is directed to a light filtering lens film. The lens films of the present invention have one or more metallized layers formed in a stack. Each metallized layer is made of a substrate with a metal coating on at least one face of the substrate. The lens film includes one or more protecting layers to provide protection against damage to the film. The lens film also includes an ultraviolet light absorbing material. In one embodiment of the invention, the ultraviolet absorbing material is an ultraviolet (UV) absorbing binder that is provided between at least two of the metallized and protecting layers together. Alternatively, the ultraviolet absorbing material is an ultraviolet absorbing layer disposed in the lens film.

In another aspect of the invention, the lens film is mounted on a base lens to provide a lens that protects the eyes of a user from harmful light irradiation.

In another embodiment of the invention, an eye protection device has a shield that covers at least the eyes of a wearer. The shield includes a lens upon which a lens film, described hereinabove, is mounted. The lens of the shield is positioned to allow the wearer of the eye protection device to look through the lens.

The lens film is used by mounting the lens film on a lens and then positioning the lens in front of a wearer's eyes so that the wearer can view the work in which the wearer is engaged. In one embodiment of the invention, the lens film is adhesively mounted to the lens.

In another aspect of the invention, a lens film is made by disposing one or more protecting layers on a metallized layer which has a metal coating disposed over a substrate. In addition, ultraviolet absorbing material is disposed in the lens film.

These and various other features which characterize the invention are pointed out with particularity in the claims annexed hereto and forming a part hereof. However, for a better understanding of the invention, its advantages and objectives obtained by its use, reference should be made to the drawings which form a further part hereof and to the accompanying descriptive matter, in which there is illustrated and described a preferred embodiment of the invention.

BRIEF DESCRIPTION OF THE DRAWINGS

Referring now to the drawings, wherein like reference numerals and letters indicate corresponding structure throughout the several views.

DETAILED DESCRIPTION OF THE INVENTION

Figure 1:
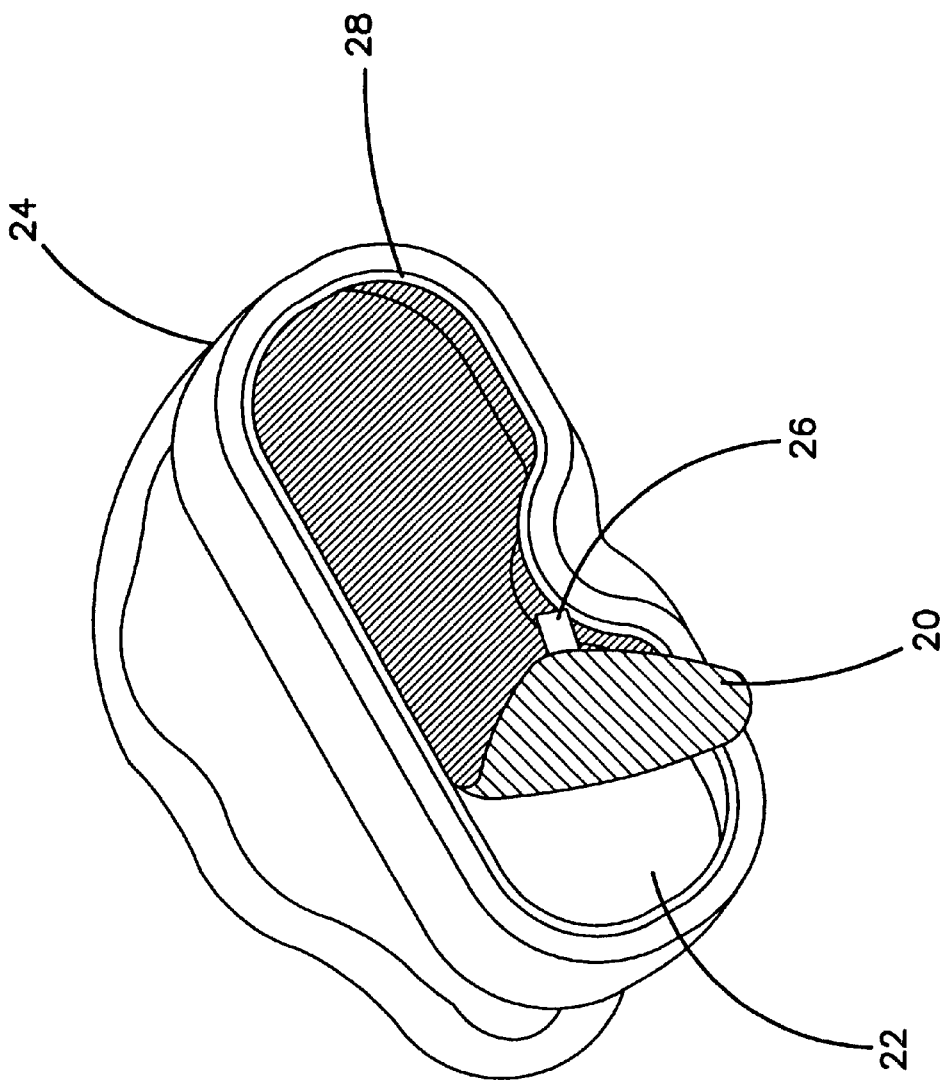
FIG. 1 shows a perspective view of an eye protection device with a lens film in accordance with the principles of the present invention partially mounted on a lens.

Referring to the Drawings, in general, FIG. 1 illustrates a lens film 20 of the invention mounted on a lens 22 of an eye protection device 24. Lens film 20 provides protection from harmful visible, infrared (IR), and ultraviolet (UV) light. In a preferred embodiment of the invention, lens film 20 meets or exceeds the transmittance requirements for a specific shade rating outlined by the American National Standards Institute, Inc. in the *American National Standard Practice for Occupational and Educational Eye and Face Protection,* ANSI Z87.1-1989.

Lens film 20 can be shaped to fit the lens or lenses of almost any type of eye protection device including goggles, spectacles, face shields, masks, or helmets. In particular, lens film 20 can be used with goggles, masks, helmets, and other eye protection devices for welding applications. Lens film 20 can be configured to fit existing eye protection devices, including those associated with other protective devices such as respirators, to provide convenient protection against harmful or intense light. It is recommended that users of lens film 20 follow the ANSI guidelines with respect to the choice of an appropriate shade rating for their activity and the choice of appropriate eyewear to provide impact protection as well as other safety procedures and guidelines.

Lens film 20 is mounted on lens 22 using an adhesive, clips, or other mounting method or device known to those skilled in the art. Lens film 20 is configured to be either permanently or, preferably, detachably mountable on lens 22. More preferably, lens film 20 is detachably mountable and remountable on lens 22. A wearer of an eye protection device having a detachably mounted lens film 20 can conveniently switch from activities involving harmful light, such as welding, to other activities by removing the lens film. If lens film 20 is remountable, then lens film 20 may be reused one or more times before it is discarded.

Lens film 20 optionally includes a graspable tab 26 with which a user can easily detach lens film 20 from lens 22. Tab 26 may be made from the same material as lens film 20, or tab 26 may be formed from other materials, such as polymers or plastics, and attached to lens film 20. A tab is only one example of a device that may be attached to the lens film to facilitate the removal of the lens film from the lens. Those skilled in the art will recognize that there are many other methods or devices for removing the lens film from the lens which are within the scope of this invention.

A further optional component that may be part of lens film 20 or may be separately applied to lens 22 is a light seal 28 which is disposed around the periphery of lens 22. When lens film 20 is applied to lens 22, lens film 20 should at least partially overlap light seal 28. The function of light seal 28 is to prevent harmful light from passing through points at the periphery of lens 22 which are not covered by lens film 20 due to, for example, an imprecise fit between lens film 20 and lens 22. Light seal 28 is formed using an opaque material and positioned on lens 22 so that lens film 20 overlaps with light seal 28 at all or nearly all points along the periphery of the lens film.

Light seal 28 can be made by painting a portion of the periphery of lens 22 with an opaque material. Light seal 28 can also be formed by adhesively attaching opaque material to the periphery of lens 22. For example, opaque polyester may be cut in the form of a frame and attached to lens 22 or, alternatively, a clear polyester sheet with a printed opaque frame may be applied to lens 22.

Figure 5:
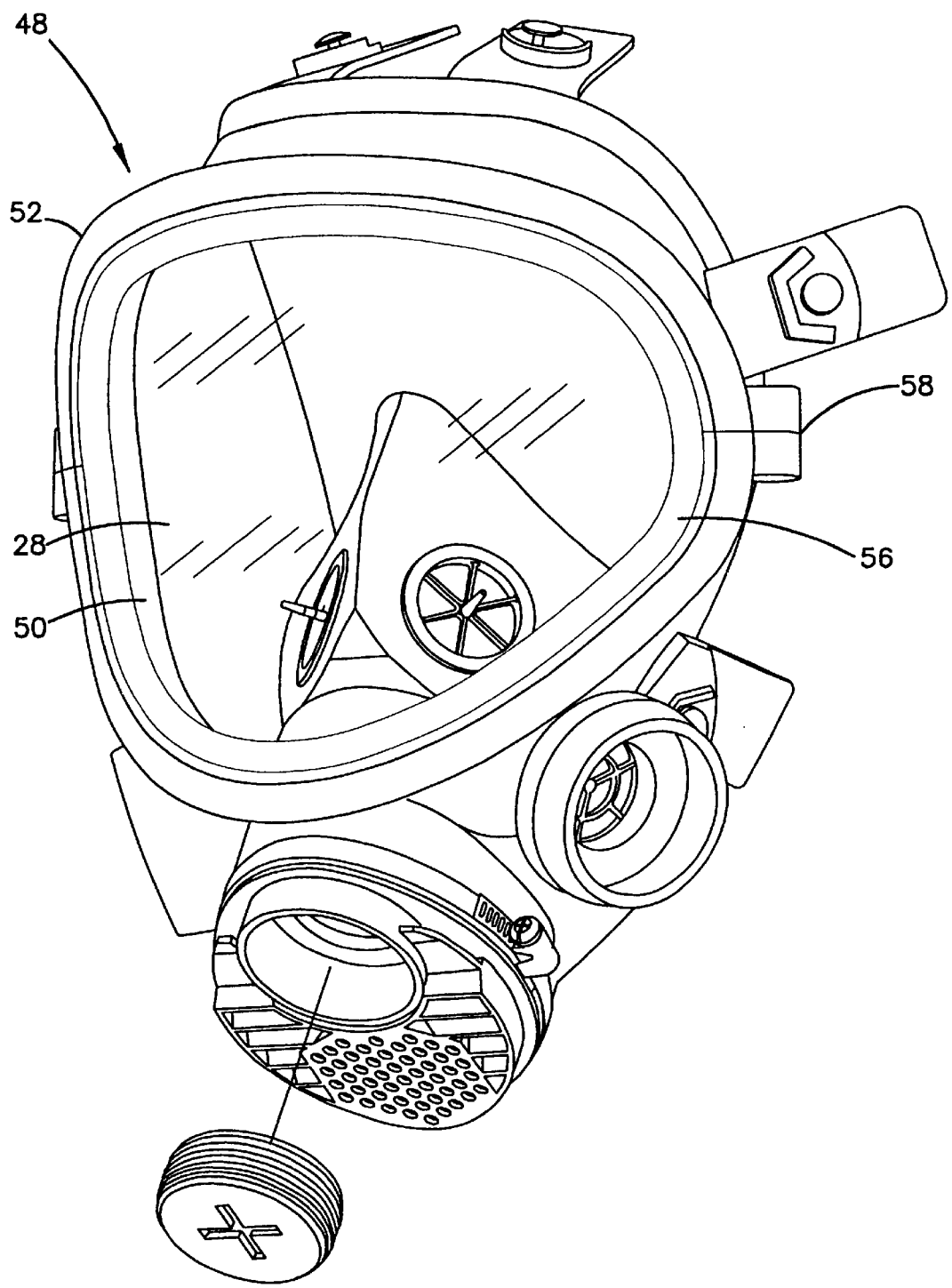
FIG. 5 shows a perspective view of a full-face respirator mask with a lens film in accordance with the principles of the present invention mounted on a lens of the mask.
Figure 6:
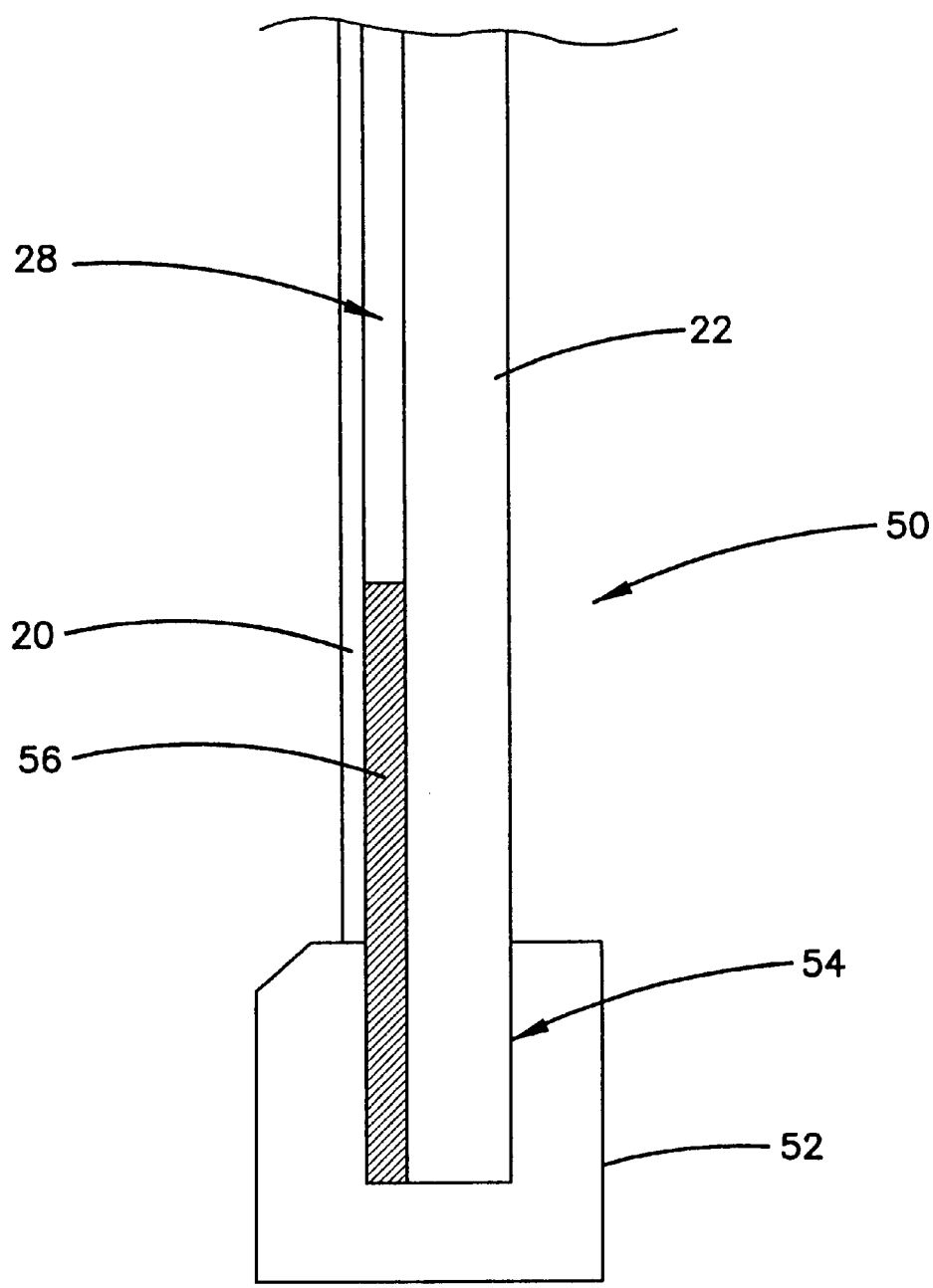
FIG. 6 shows a partial side-sectional view of the lens region of the mask of FIG. 5.

In one embodiment of the invention, illustrated in FIGS. 5 and 6, light seal 28 is attached to lens 22 of an eye protection device 48, such as the full-protection respirator mask shown in FIG. 5. A typical full-protection respirator mask 48 is a 3M model 7800 respirator, available from Minnesota Mining and Manufacturing Company ("3M"), St. Paul, Minn. A lens assembly 50, shown in detail in FIG. 6, includes lens 22, lens film 20, and light seal 28, and is held within a channel 54 of a clamping flange 52. The flange 52 is fastened to mask 48 by a flange securement means 58, such as screws or other fasteners, to prevent slippage of lens assembly 50. Light seal 28, in this embodiment of the invention, is typically a thin film which has an opaque region 56 that extends radially inward from the edge of light seal 28 to cover the exposed periphery of lens 22, as shown in FIG. 6. Lens film 20 is applied over light seal 28 so that it overlaps with the light seal.

Light seal 28 is held in place by the clamping action of flange 52. Optionally, light seal 28 may also be adhesively bonded to lens 22. In addition, lens film 20 is adhesively bonded to light seal 28, although other means of binding lens film 20 to light seal 28 and/or lens 20 are also within the scope of this invention.

In an alternative embodiment of the invention, light seal 28 is a layer of peripherally opaque material which is attached to or part of the layered structure of lens film 20, discussed hereinbelow. For example, light seal 28 may be an opaque polymeric ring attached to the periphery of lens film 20 so that when lens film 20 is mounted on lens 22, light seal 28 overlaps the periphery of both lens film 22 and lens 20.

Figure 2:
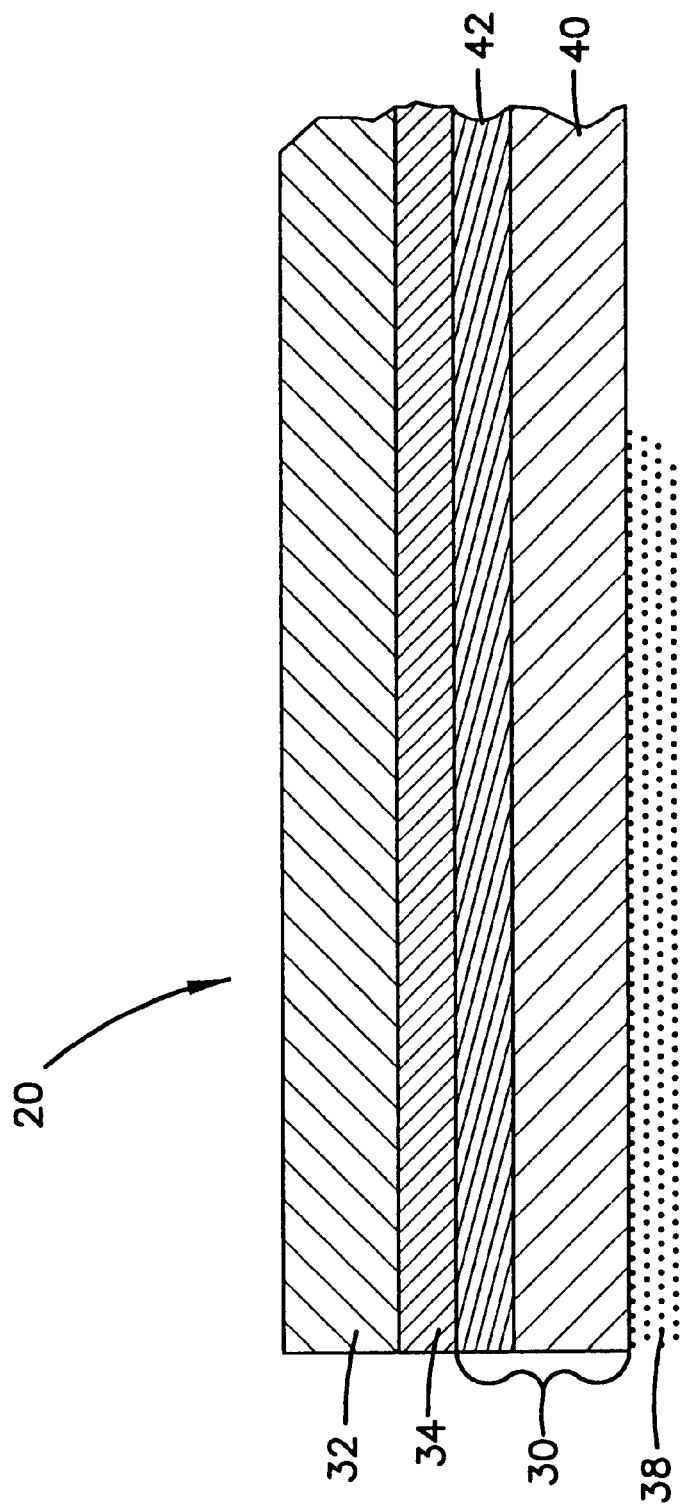
FIG. 2 shows a side-sectional view of a first embodiment of a lens film in accordance with the principles of the present invention, in which the lens film has one protecting layers one metallized layer.
Figure 3:
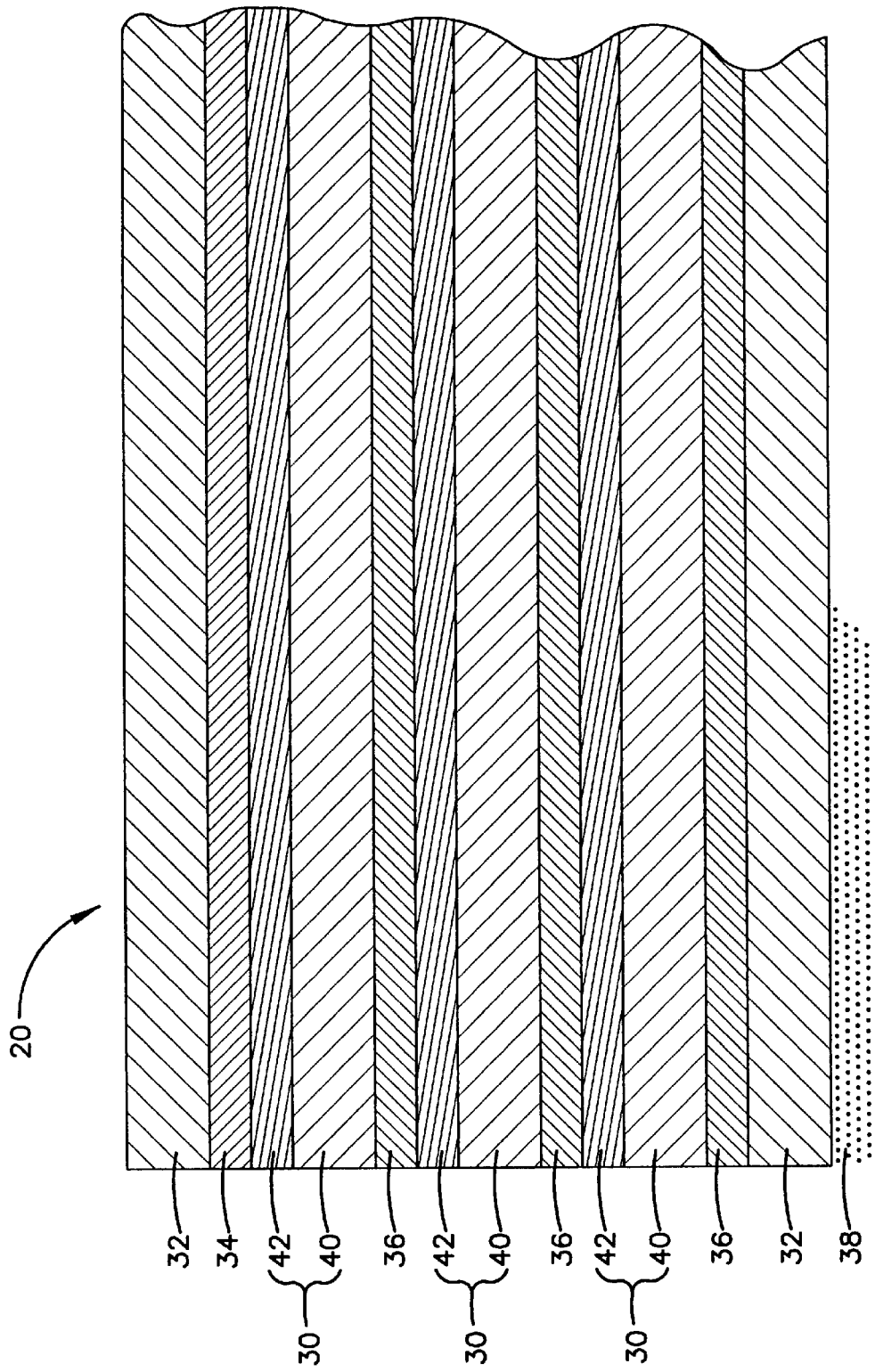
FIG. 3 shows a side-sectional view of a second embodiment of a lens film in accordance with the principles of the present invention having two protecting layers and three metallized layers.
Figure 4:
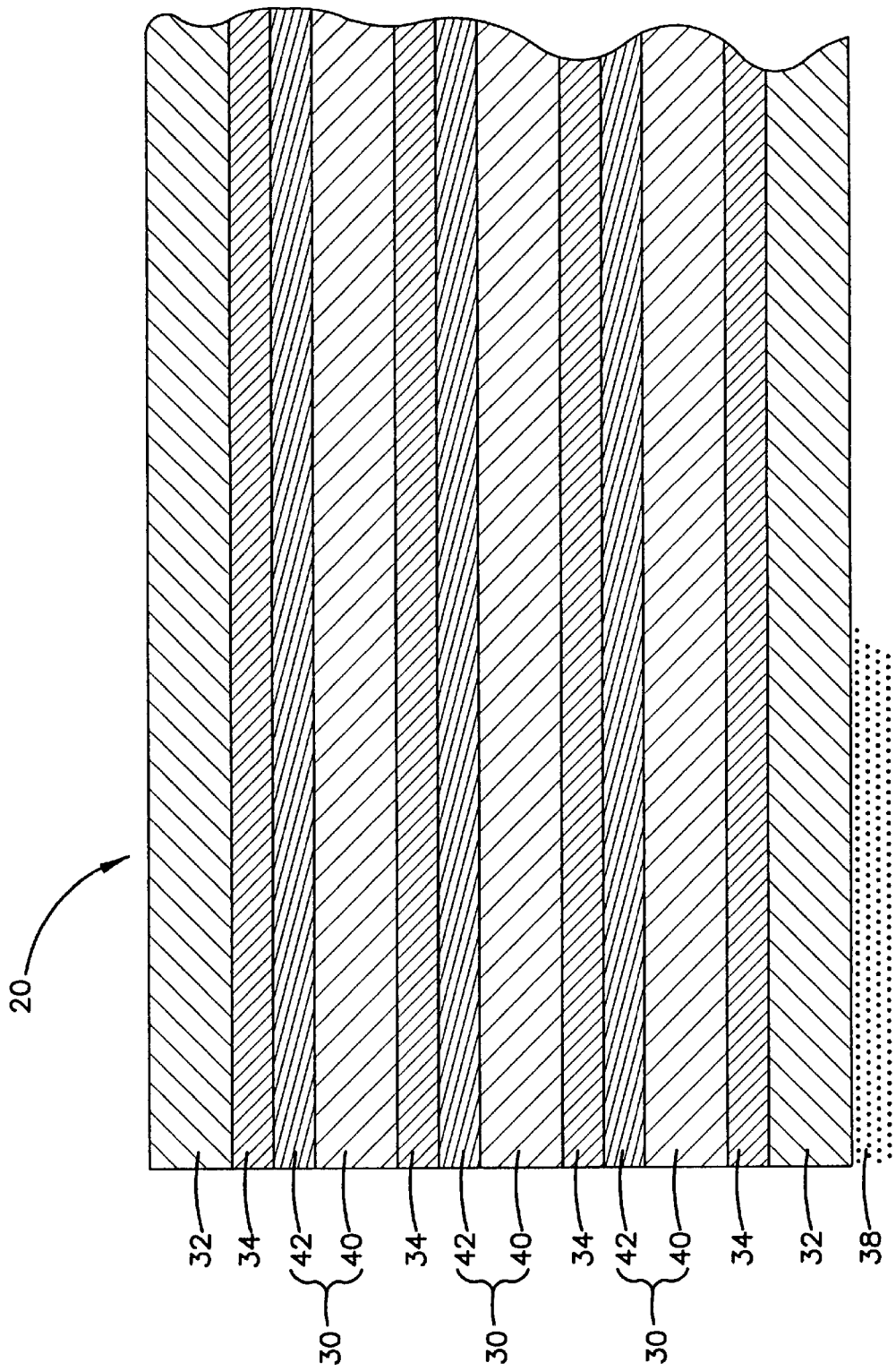
FIG. 4 shows a side-sectional view of a third embodiment of a lens film in accordance wit the principles of the present invention having two protecting layers and three metallized layers with UV absorbing binder between all of the layers.

Lens film 20 is a layered composite as depicted in FIGS. 2–4. Preferably, the layers forming lens film 20 are thin so that the lens film is flexible and can conform to the contours of the lens to which the lens film is to be attached. Lens film 20 typically includes one or more metallized layers 30 and one or more protecting layers 32. These layers are held together to form a stack of layers by a lamination adhesive 36 which may optionally be a UV absorbing binder 34. Optionally, a layer of mounting adhesive 38 is applied to a portion of lens film 20 so that lens film 20 can be adhesively mounted on a lens 22.

The metallized layers 30 have a substrate 40 covered on at least one surface by a thin metal coating 42. The metal coating 42 typically reflects or absorbs visible and infrared light. Metal coating 42 is usually formed from a reflective metal or alloy such as aluminum, copper, gold, silver, titanium, inconel, or stainless steel, which is vapor-coated or sputtered on substrate 40. Suitable metallized layers are available commercially (for example, 3M-brand Scotchtint™ metallized films from 3M).

Substrate 40 of metallized layer 30 is often a polymer film although other suitable substrates may also be used. Suitable polymer films are made from acrylic polymers, such as acrylate, methacrylate, and copolymers thereof; polyethylene and copolymers thereof; polypropylene and copolymers thereof; polyvinylchloride and copolymers thereof; nylon; polycarbonate; and polyesters, such as polyethylene terephthalate, as well as other polymers known to those skilled in the art. Such polymeric films are well-known in the art and are commercially available in thicknesses ranging from less than 0.5 mils to more than 10 mils (1 mil equals 0.001 inch).

In addition to providing support for metal coating 42, substrate 40 may also absorb harmful irradiation such as ultraviolet light. Moreover, substrate 40 may be tinted to provide further light absorption.

Furthermore, lens film 20 may contain multiple metallized layers 30 stacked together, as shown in FIGS. 3 and 4, to increase the amount of eye protection beyond that of each individual metallized layer. The metal coatings and substrates of the multiple metallized layers of lens film 20 need not be constructed of the same materials. These layers can be stacked together to produce a lens film having a specific shade rating. Typically, the stacking of metallized films produces a lens film that has light transmittance greater than initially expected based on the transmittance of each individual film.

Protecting layers 32 are provided on lens film 20 to protect the underlying layers from scratching and damage. These layers are typically a polymer film formed from acrylic polymers, such as acrylate, methacrylate, and copolymers thereof; polyethylene and copolymers thereof; polypropylene and copolymers thereof; polyvinylchloride and copolymers thereof; nylon; polycarbonate; and polyesters, such as polyethylene terephthalate, as well as other suitable polymers known to those skilled in the art. Protecting layers 32 may be provided separately on lens film 20 or, alternatively, substrate 40 of one or more of the metallized layers may also act as a protecting layer.

Typically, there is at least one protecting layer disposed over the surface of lens film 20 as shown in FIG. 2. This protecting layer 32 is preferably made of a material which is heat resistant to protect lens film 20 from heat generated by activities such as welding. Optionally, a protecting layer may be disposed on the other surface of lens film 20 as shown in FIGS. 3 and 4 to provide scratch resistance to this surface.

Layers other than metallized layers and protecting layers may be included in lens film 20. For example, a tinted layer for removing visible light or an ultraviolet absorbing layer may be included among the metallized and protecting layers of lens film 20. These layers are typically made from the same materials as the protecting layers and/or metallized layers.

Lens film 20 also includes ultraviolet absorbing material. In one embodiment of the invention, substrate 40 of one or more of the metallized layers 30 contains UV absorbing material. The substrate may be UV absorbing due to the inherent properties of the substrate material. For example, polyester absorbs some ultraviolet light. Alternatively, a UV absorbing compound may be added to the substrate material or coated on the substrate.

Figure 7:
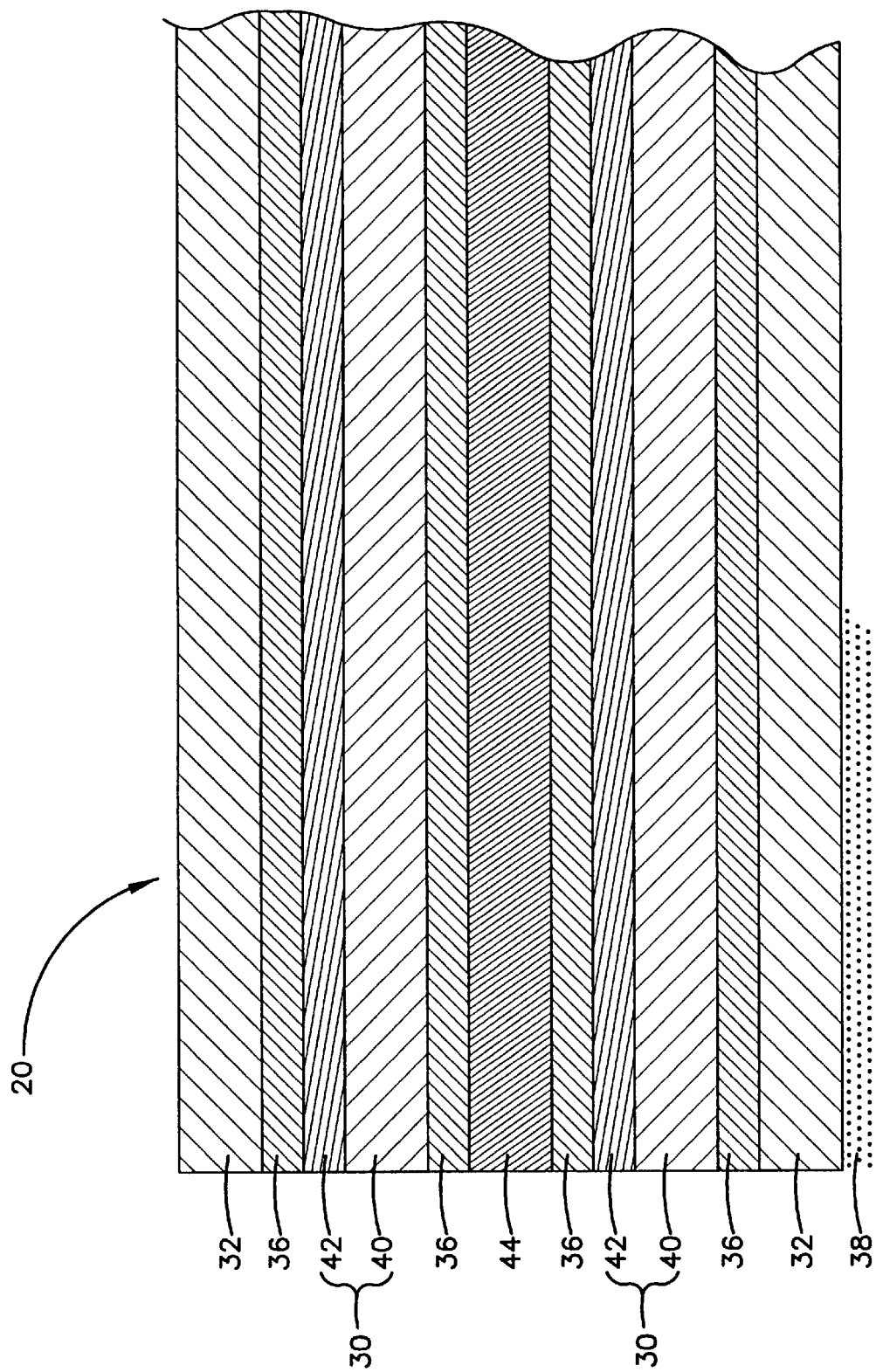
FIG. 7 shows a side-sectional view of a fourth embodiment of a lens film in accordance with the principles of the invention having two protecting layers, two metallized layers, and one UV absorbing layer.

Alternatively, as shown in FIG. 7, one or more separate UV absorbing layers 44 might be provided within the stack of layers that make up lens film 20. This additional layer may be made of UV absorbing material or may contain one or more UV absorbing compounds as an additive to or coating on a substrate material. The UV absorbing layer can be made from the same polymeric materials as the protecting layers or the substrates of the metallized layers.

In another embodiment of the invention, shown in FIGS. 2–4, the UV absorbing material is a UV absorbing binder 34. UV absorbing binder is typically an adhesive containing one or more UV absorbing compounds. Examples of UV absorbing compounds for use in a UV absorbing binder or for incorporation in a UV absorbing layer include substituted benzophenones and substituted benzotriazoles. Examples of suitable substituted benzophenones include 2,4-dihydroxybenzophenone; 2-hydroxy-4-acryloxyethoxybenzophenone; 2-hydroxy-4-methoxy-benzophenone; 2,2'-dihydroxy-4-methoxy-benzophenone; 2,2'-dihydroxy-4,4'-dimethoxy-benzophenone; 2-hydroxy-4-n-octyloxy-benzophenone; 2,2',4,4'-tetrahydroxy-benzophenone; and 4-dodecyloxy-2-hydroxy-benzophenone. Suitable benzotriazoles include 2-[2'-hydroxy-3',5'-di(a,a-dimethyl-benzyl) phenyl]-benzotriazole, 2-(2'-hydroxy-5'-methylphenyl)-benzotriazole, 2-(3',5'-di-t-butyl-2'-hydroxyphenyl)-5-chlorobenzotriazole, 2-(3'-t-butyl-2'-hydroxy-5'-methylphenyl)-5-chlorobenzotriazole, 2-(2'-hydroxy-3',5'-di-t-butylphenyl)-benzotriazole, 2-(2'-hydroxy-5'-t-octylphenyl)-benzotriazole, and 2-(2'hydroxy-3',5'-di-tertiary amylphenyl)-benzotriazole. Any of these or other suitable UV absorbing compounds may be used alone or in combination to provide the desired UV absorption.

In this embodiment of the invention, UV absorbing binder is provided between at least two of the protecting and metallized layers. Preferably, UV absorbing binder 34 is provided between all of the protecting and metallized layers, as shown in FIG. 4.

Lens film 20 also optionally includes a mounting adhesive 38 applied to a portion of the lens film. Preferably, mounting adhesive 38 is applied to a portion of the periphery of lens film 20 to minimize the surface of lens 22 in contact with mounting adhesive 38 as the adhesive may cause visual distortions.

Mounting adhesive 38 may be a contact adhesive, such as adhesive tape or pressure sensitive adhesive, or may require water or another solvent to activate or expose the adhesive. Preferably, mounting adhesive 38 provides for detachable mounting of lens film 20 to lens 22 and more preferably, mounting adhesive 38 provides for remounting of lens film 20. Optionally, a removable adhesive protection strip, not shown, is provided over the mounting adhesive 38 to prevent unwanted adhesion of the lens film to other objects.

EXAMPLES

The following examples demonstrate the principles of the invention. It is to be understood that these examples are merely illustrative and are in no way to be interpreted as limiting the scope of the invention.

Three lens films having a shade rating of 4 or better were made following the principles of the invention. The three lens films had the following configurations:

| Film 1 | Film 2 | Film 3 |
|---|---|---|
| SCLARL400 | SCLARL400 | SCLARL400 |
| LE30CUARL | LE30CUARL | LE30CUARL |
| LE30CUARL | LE30CUARL | LE30CUARL |
| LE30CUARL | LE20SIAR | NR35SMARL |
| Mylar™ | Mylar™ | LE30CUARL |
|  |  | Mylar™ |

SCLARL400 (3M) is a 0.005" thick polymeric protecting layer which provided scratch and heat resistance to the lens film. LE30CUARL and LE20SIAR are Scotchtint™ metallized films (3M) with copper and aluminum coatings, respectively, on a tinted polyester substrate. NR35SMARL is a tinted polyester film (3M). A.0.004" Mylar™ film was applied to the back surface of the stack of metallized layers to provide protection against scratching. The layers were held together by a UV absorbing binder which is provided on the commercially available films. An adhesive transfer tape (3M, No. Y920XL) was applied over a portion of the Mylar™ layer so that the lens film could be adhesively mounted on a lens. The lens film was cut using scissors in an approximately oval shape for use with lenses of a full-face respirator providing eye protection. When the lens film was cut, a tab of material was left attached to the oval lens film to provide a convenient method for detaching the lens film from a lens.

The transmittance of these lens films was measured over the range of 200 to 2000 nm. The weighted transmittances of the films were then calculated as described in the ANSI standards, ANSI Z87.1-1989, 24–25, for the luminous (380–780 nm), far ultraviolet (200–315 nm), near ultraviolet (315–385 nm), infrared (780–2000 nm), and blue (400–1400 nm) spectra. The results, as well as the requirements for a Shade 4 and 5 protective lens, are presented in Table 1.

TABLE 1

Weighted Transmittances (%) for Films 1–3

| | Shade 4 | Shade 5 | Film 1 | Film 2 | Film 3 |
|---|---|---|---|---|---|
| $T_L$ (380–780 nm) | 3.16–8.50 | 1.18–3.16 | 4.8 | 2.7 | 1.5 |
| $T_{NUV}$ (315–385 nm) | $<T_L/10$ | $<T_L/10$ | <0.1 | <0.1 | <0.1 |
| $T_{FUV}$ (200–315 nm) | <0.04 | <0.02 | <0.01 | <0.01 | <0.01 |
| $T_{IR}$ (780–2000 nm) | <5.0 | <2.5 | 0.6 | 0.5 | 0.6 |
| $T_{blue}$ (400–1400 nm) | $<T_L$ | $<T_L$ | 2.1 | 2.1 | 0.7 |

The test data shown in Table 1 show that lens film 1 meets the requirements for a Shade 4 rating and lens films 2 and 3 meet the requirements for a Shade 5 rating. In addition, these lens films were flexible and could be cut to a desired shape to fit a lens of an eye protection device. The mounting adhesive applied to these lens films also provided for detachable mounting and remounting of the lens film on an appropriate lens.

The invention has been described with reference to various specific and preferred embodiments and techniques. However, it will be apparent to one of ordinarily skill in the art that many variations and modifications may be made while remaining within the spirit and scope of the invention.

All publications in this specification are indicative of the level of ordinary skill in the art to which this invention pertains. All publications are herein incorporated by reference to the same extent as if each individual publication or patent application was specifically and individually indicated by reference.

What is claimed is:

1. A lens film for attachment to a transparent lens, comprising:
   one or more metallized layers, each metallized layer comprising a substrate and a metal coating on one face of the substrate, the metallized layers being arranged in a stack;
   one or more protecting layers disposed over at least one face of the stack of metallized layers; and
   an ultraviolet light absorbing material disposed between one or more layers of the lens film wherein said film is flexible, and suitable for use against light hazards in welding.

2. The lens film of claim 1, wherein the substrate of at least one metallized layer acts as a protecting layer.

3. The lens film of claim 1, wherein the film further comprises an at least partially opaque layer attached to a metallized layer or a protecting layer, wherein the at least partially opaque layer comprises opaque material disposed at the periphery of the lens film.

4. The lens film of claim 1, wherein the lens film further comprises means for attaching the lens film to a lens.

5. The lens film of claim 1, wherein the lens film comprises at least two protecting layers and wherein at least one protecting layer is disposed on each face of the stack of metallized layers.

6. The lens film of claim 1, wherein the substrate of at least one metallized layer is tinted.

7. The lens film of claim 1, wherein the lens film is flexible.

8. The lens film of claim 1, wherein at least one of the protecting layers is heat resistant.

9. A lens film for attachment to a transparent lens, comprising:
   one or more metallized layers, each metallized layer comprising a substrate and a metal coating on one face of the substrate, the metallized layers being arranged in a stack;
   one or more protective layers disposed over at least one face of the stack of metallized layers; and
   an ultraviolet light absorbing material disposed between one or more layers of the lens film wherein said film is flexible and suitable for use against light hazards in welding and wherein the ultraviolet light absorbing material includes an ultraviolet light absorbing binder disposed between at least two of the metallized or protecting layers.

10. The lens film of claim 9, wherein ultraviolet absorbing binder is disposed between all of the metallized and protecting layers of the lens film.

11. A lens film for attachment to a transparent lens, comprising:
   one or more metallized layers, each metallized layer comprising a substrate and a metal coating on one face of the substrate, the metallized layers being arranged in a stack;
   one or more protective layers disposed over at least one face of the stack of metallized layers; and
   an ultraviolet light absorbing material disposed between one or more layers of the lens film wherein said film is flexible and suitable for use against light hazards in welding and wherein said lens film further comprises adhesive covering a portion of one surface of the lens film for attaching said lens film to a lens.

12. The lens film of claim 11, wherein the adhesive provides for detachably mounting the lens film on the lens.

13. The lens film of claim 12, wherein the lens film further comprises a graspable tab attached to the lens film.

14. The lens film of claim 12, wherein the lens film is remountable.

15. A lens for providing optical protection in welding applications, comprising:
   a base lens; and
   a lens film mounted on the base lens, the lens film comprising:
      one or more metallized layers, each metallized layer comprising a substrate and a metal coating on one face of the substrate, the metallized layers being arranged in a stack;

one or more protecting layers disposed over at least one face of the stack of metallized layers; and an ultraviolet light absorbing material disposed in the lens film.

16. The lens of claim 15, wherein the lens film is detachably mounted on the base lens.

17. The lens of claim 16, wherein the lens film is remountable.

18. The lens of claim 15, wherein the lens further comprises a light seal having opaque material disposed around the periphery of the base lens.

19. A lens for providing optical protection in welding applications, comprising:

a base lens; and a lens film mounted on the base lens, the lens film comprising:

one or more metallized layers each metallized layer comprising a substrate and a metal coating on one face of the substrate, the metallized layers being arranged in a stack;

one or more protective layers disposed over at least one face of the stack of metallized layers; and an ultraviolet light absorbing material disposed in the lens film, wherein the lens film is adhesively mounted on the base lens.

20. An eye protection device, comprising:

a shield configured for covering at least the eyes of a wearer, wherein the shield comprises a lens positioned to allow the wearer of the eye protection device to look through the lens; and a flexible lens film mounted on the lens, the lens film comprising:

one or more metallized layers, each metallized layer comprising a substrate and a metal coating on one face of the substrate, the metallized layers being arranged in a stack;

one or more protecting layers disposed over at least one face of the stack of metallized layers; and ultraviolet light absorbing material disposed in the lens film.

21. The eye protection device of claim 20, wherein the lens film is detachably mounted on the lens.

22. The eye protection device of claim 21, wherein the lens film is remountable.

23. The eye protection device of claim 22, wherein the lens further comprises a light seal having opaque material disposed around the periphery of the base lens.

24. The eye protection device of claim 23, wherein the light seal is clamped to the lens.

25. An eye protection device, comprising:

a shield configured for covering at least the eyes of a wearer, wherein the shield comprises a lens positioned to allow the wearer of the eye protection device to look through the lens; and a flexible lens film mounted on the lens, the lens film comprising:

one or more metallized layers each metallized layer comprising a substrate and a metal coating on one face of the substrate, the metallized layers being arranged in a stack;

one or more protective layers disposed over at least one face of the stack of metallized layers; and ultraviolet light absorbing material disposed in the lens film wherein the lens film is adhesively mounted on the lens.

* * * * *